United States Patent [19]

Liepmann et al.

[11] 4,170,649
[45] Oct. 9, 1979

[54] 1,4-BENZODIAZEPINE DERIVATIVES, PHARMACEUTICAL COMPOSITIONS THEREOF, AND PROCESS FOR THEIR PREPARATION

[75] Inventors: Hans Liepmann; Rolf Hueschens, both of Hanover; Wolfgang Milkowski, Burgdorf; Horst Zeugner, Hanover; Renke Budden, Hanover; Jacqueline Bahlsen, Hanover, all of Fed. Rep. of Germany

[73] Assignee: Kali-Chemie Pharma GmbH, Hanover, Fed. Rep. of Germany

[21] Appl. No.: 996,720

[22] Filed: Dec. 5, 1978

[30] Foreign Application Priority Data

Dec. 5, 1977 [DE] Fed. Rep. of Germany ....... 2754112

[51] Int. Cl.$^2$ ..................... A61K 31/55; C07D 243/16
[52] U.S. Cl. ............................. 424/244; 260/239 BD; 260/239.3 D
[58] Field of Search ................... 260/239 BD; 424/244

[56] References Cited

U.S. PATENT DOCUMENTS

| | | | |
|---|---|---|---|
| 3,998,209 | 12/1976 | Milkowski et al. | 260/239 BD |
| 4,096,141 | 6/1978 | Milkowski et al. | 260/239 BD |
| 4,125,726 | 11/1978 | Walser et al. | 548/324 |

FOREIGN PATENT DOCUMENTS

| | | | |
|---|---|---|---|
| 2221536 | 11/1973 | Fed. Rep. of Germany ... | 260/239.3 D |
| 2540222 | 4/1976 | Fed. Rep. of Germany ... | 260/239 BD |

*Primary Examiner*—Alton D. Rollins
*Attorney, Agent, or Firm*—Schwartz, Jeffery, Schwaab, Mack, Blumenthal & Koch

[57] ABSTRACT

New 1,4-benzodiazepine derivatives are disclosed which are substituted in 2-position by cyanomethylene or carbamoylmethylene and have the formula

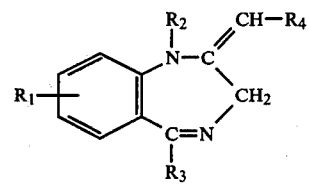

wherein $R_1$ represents hydrogen, halogen, or nitro, $R_2$ represents hydrogen or lower alkyl, $R_3$ represents phenyl which may be substituted by halogen or $CF_3$, and $R_4$ represents cyano or carbamoyl. The compounds exhibit tranquilizing activities. The cyanomethylene-compounds are prepared by oxidizing corresponding cyanomethyl compounds with Cr-VI-oxide in an acidic reaction medium. The cyanomethylene-group can subsequently be hydrolyzed into the carbamoylmethylene group.

19 Claims, No Drawings

1,4-BENZODIAZEPINE DERIVATIVES, PHARMACEUTICAL COMPOSITIONS THEREOF, AND PROCESS FOR THEIR PREPARATION

BACKGROUND OF THE INVENTION

The present invention relates to new 1,4-benzodiazepine-derivatives, which are substituted by a cyano- or carbamoyl-substituted methylene group in 2-position of the benzodiazepine structure, processes for their preparation and pharmaceutical compositions thereof. The German Offenlegungsschrift No. 2,221,558 and the corresponding U.S. Pat. No. 3,998,809 disclose 1,4-benzodiazepine-derivatives which are substituted by a substituted methyl group in 2-position of the benzodiazepine structure, and which possess anti-convulsive, sedative, and muscle-relaxing properties.

From the German Offenlegungsschrift No. 2,221,536 it is known that if 1,4-benzodiazepine-derivatives which are substituted by a substituted methyl group in 2-position are treated with an oxidizing agent, the side-chain in 2-position is split off and the compounds are oxidized into 1,4-benzodiazepine-2-one derivatives.

SUMMARY OF THE INVENTION

It is an object of the present invention to provide new pharmacologically-active 1,4-benzodiazepine-derivatives and pharmaceutical compositions thereof which possess improved central-nervous-system-depressant activities and, in particular, possess improved tranquilizing and anti-spasmodic, muscle-relaxing, and anti-aggressive activities. It is a further object of the present invention to provide such compounds and compositions which are low in side-effects and toxicity and exhibit a high therapeutic index.

It is a further object of the present invention to provide a process for preparing such new 1,4-benzodiazepine-derivatives with improved pharmacological properties.

In order to accomplish the foregoing objects according to the present invention there are provided new 1,4-benzodiazepines of the formula I

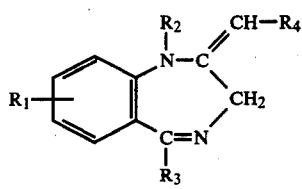

wherein
$R_1$ represents hydrogen, halogen, or nitro;
$R_2$ represents hydrogen, or lower alkyl;
$R_3$ represents phenyl, or phenyl which is substituted by halogen or trifluoromethyl; and
$R_4$ represents cyano or carbamoyl
and pharmaceutically-acceptable acid addition salts thereof.

These compounds exhibit valuable pharmacological properties, in particular improved central-nervous-system-depressant and tranquilizing properties due to which they are useful as tranquilizers, and in the treatment of stress- and anxiety-induced neurotic disorders. The foregoing pharmacological properties are particularly outstanding in compounds wherein $R_4$ represents carbamoyl.

According to the present invention there are further provided pharmaceutical compositions comprising a sedatively-effective amount of the above-defined compounds and a pharmaceutically acceptable diluent.

According to the present invention there are further provided processes for preparing the compounds of formula I in good yields. According to the present invention, compounds of formula Ia

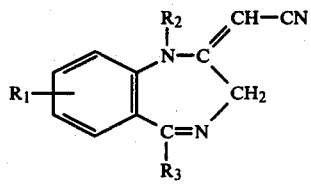

wherein $R_1$, $R_2$, and $R_3$ are as defined above, can be prepared by a process which comprises oxidizing a compound of formula II

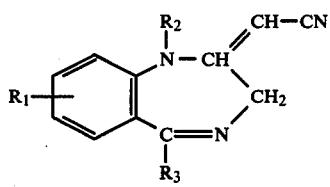

in an acidic reaction-mixture with an oxidizing-agent comprising a chromium-VI-compound which is chromium-VI-oxide, chromic acid or a mixture thereof at least partially dissolved in an acidic solvent.

The above compounds of formula Ia can be further hydrolyzed into the compounds of formula Ib.

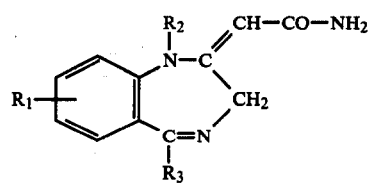

The compounds of formula I may be recovered from the respective reaction-solutions in form of the free-bases or in the form of their acid-addition-salts. Acid-addition-salts may be transformed into free bases and vice versa according to conventional methods.

Further objects, features, and advantages of the present invention will become apparent from the detailed description of the invention which follows.

DETAILED DESCRIPTION OF THE INVENTION AND ITS PREFERRED EMBODIMENTS

It has been found that the above-defined compounds of formula I possess the above-mentioned pharmacological activities, and at the same time are low in side-effects and toxicity, and thus exhibit a high therapeutic index.

If in the compounds of formula I $R_2$ represents lower alkyl, this lower alkyl may be straight or branched and may comprise 1 to about 6, preferably 1 to about 3 carbon atoms. Preferred lower alkyl groups are methyl, ethyl, n-propyl or isopropyl. Other suitable alkyl groups include n-butyl, isobutyl, sec.-butyl, tert.-butyl, and n-pentyl. Further examples of lower alkyl groups are isopentyl, 2-methylbutyl, pentyl, 1-methylbutyl, 1,2-dimethylpropyl, tert.-pentyl, n-hexyl, or isohexyl.

Halogen-substituents within the compounds of formula I may be chlorine, bromine, iodine or fluorine.

Preferably the substituent $R_1$ is situated in 7-position of the 1,4-benzodiazepine-structure. A preferred group of compounds of formula I includes compounds wherein $R_1$ is in 7-position and/or $R_2$ is methyl and/or $R_3$ represents phenyl, o-halogenophenyl or o-trifluoromethylphenyl.

The 2-cyanomethylene compounds of formula Ia are prepared by oxidizing the corresponding 2-cyanomethyl-compound of formula II, and the 2-carbamoylmethyl-compounds of formula Ib are obtained by hydrolyzing the corresponding 2-cyanomethyl-compounds of formula Ia. Both these reactions are surprising. It could not be expected that the 2-cyanomethyl-group could be oxidatively transformed into the 2-cyanomethylene-group, and it also could not be foreseen that the 2-carbamoylmethylene-group could be obtained in good yields by hydrolysis of the 2-cyanomethylene-group.

As mentioned above, it is known from the German Offenlegungsschrift No. 2,221,536 that oxidation of 1,4-benzodiazepine-derivatives which are substituted by a substituted methyl-group in position 2 leads to splitting-off of the side-chain in 2-position and to formation of the corresponding 1,4-benzodiazepine-2-one. Suitable oxidizing-agents for this reaction are potassiumpermanganate, manganese dioxide, chromium trioxide, or dichromate salts, whereby potassiumpermanganate is preferred. Reacting the 2-cyanomethyl-compounds of formula II with potassiumpermanganate in an aqueous hydrochloric acid-solution also leads to the corresponding 1,4-benzodiazepine-2-one-derivatives in good yields, whereby unsaturated nitriles of formula I can be detected only in minor amounts.

It has now been found that by treating the 2-cyanomethyl-compounds of formula II with chromic acid under the above-defined reaction-conditions, unsaturated nitriles of formula I are obtained in good yields. This is surprising since it has also been found that these unsaturated nitriles can easily be oxidized with potassiumpermanganate in an acidic solution to form the corresponding 1,4-benzodiazepine-2-one-derivatives.

Preferably chromium-(VI)-oxide in an acidic solution is used as oxidizing-agent in the process according to the present invention. However, other chromium-(VI)-compounds which are capable of forming chromic acid in situ in the acidic reaction-medium can also be used. Such compounds are, in particular, alkali metal chromates or alkali metal dichromates. The reaction-medium preferably is adjusted to the optimum acidic pH-value by adding an inorganic acid, preferably a strong mineral acid such as hydrochloric acid or sulfuric acid.

The oxidizing-agent preferably is applied in form of a solution or in form of a finely distributed suspension in a solution of the starting material of formula II.

The starting-materials of formula II suitably are dissolved in an inert organic solvent. Such suitable solvents include dimethyl formamide, preferably aromatic hydrocarbons, such as benzene, toluene, or xylene, tertiary organic bases such as pyridine, halogenated hydrocarbons, such as methylene chloride or chloroform, lower carboxylic acids, such as acetic acid or propionic acid, or mixtures of these solvents. These solvents may also be used in admixture with water in a one-phase or a two-phase reaction-mixture.

The reaction-temperature for the oxidation suitably is in the range of between 0° and 50° C., however, in some instances higher temperatures might be required.

For example, good yields in unsaturated nitriles of formula Ia are obtained if a solution of chromium-(VI)-oxide in a hydrochloric- or sulfuric-acid-solution is used as oxidizing agent, glacial acetic acid is used as an organic solvent, and the reaction is carried out at a temperature of between about 10° and about 20° C.

The 2-cyanomethylene-1,4-benzodiazepines of formula Ia, which themselves exhibit psycho-pharmacological activities, can be hydrolized into 2-carbamoylmethylene-1,4-benzodiazepines of formula Ib, which are particularly useful as psycho-sedative agents due to their sedative activities which are shown in the pharmacological tests in animals which are described below.

It has been found that the 2-cyanomethylene group within the compounds of formula Ia can be transformed into the 2-carbamoylmethylene group by means of hydrolysis without isomerizing or attacking the exocyclic double bond. It could not be expected that under the necessary hydrolyzing reaction conditions no isomeration would take place and this double bond would not be transferred into the benzodiazepine cyclus under formation of 1H-1,4-benzodiazepine derivatives.

The hydrolysis of the cyano-group can be carried out in a conventional manner by means of strong acids like hydrochloric acid, hydrobromic acid, sulfuric acid, or else with polyphosphoric acid or boron-trifluoride. The reaction may be carried out in the presence or in the absence of an inert solvent. Suitable solvents are, for example, lower carboxylic acids, in particular acetic acid. The reaction-temperature suitably is between 0°–100° C. and may vary depending on the acid which is used as hydrolyzing agent. According to the present invention, hydrolysis of the cyano-group preferably is carried out by using concentrated sulfuric acid as hydrolyzing agent at a temperature of from about 30° to about 60° C.

The starting-materials of formula II are known in the art. These compounds may, for example, be prepared according to the method which is described in U.S. Pat. No. 3,989,809, the disclosure of which is incorporated herein by reference. According to this process an acyldiamine of formula III

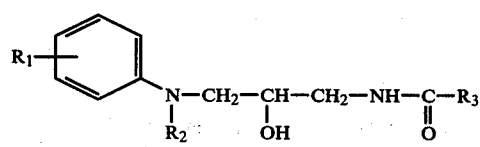

wherein $R_1$, $R_2$, and $R_3$ are as defined above, is subjected to cyclization by treating it with phosphorous oxychloride at reflux temperature and the resulting 2-chloromethyl-1,4-benzodiazepine is further reacted with potassium cyanide to form the compound of formula II.

It is to be noted, that the unsaturated nitrile of formula Ia can be further reacted into the corresponding 2-carbamoylmethylene-1,4-benzodiazepine without isolating or purifying the intermediate product.

The work-up of the reaction mixtures and isolation and/or purification of the final products, e.g., the 2-carbamoylmethylene-1,4-benzodiazepines of formula Ib, can be carried out in a conventional manner. For example, the reaction mixture can be decomposed by adding ice and the raw product can be extracted from the aqueous phase by means of a suitable organic solvent, such as, e.g., methylenechloride, chloroform, ether, acetic acid ester, toluene, or benzene. For further purification the solvent may be evaporated and the residue may be re-crystallized from a suitable solvent or mixture of solvents. Examples of suitable solvents are toluene, benzene, acetic acid ester, ethanol, and the like. It is within the knowledge of everyone skilled in the art to choose a suitable solvent depending on the dissolution-properties of the respective compound.

If desired, the compounds of formula I which are obtained by the processes according to the present invention may be transformed into acid-addition-salts with inorganic or organic acids by known methods. For example, for this purpose a solution of a compound of formula I in an organic solvent may be reacted with the desired acid which is to become a component of the acid-addition-salt. Preferably, the reaction is carried out in such an organic solvent, wherein the resulting salt is difficultly soluble in order that it can be easily separated by filtration.

Suitable such solvents are, for example, ethanol, isopropanol, ether, acetone, methylethylketone, acetone/ether, aceton/ethanol, or ethanol/ether.

The new compounds of formula I according to the present invention and their pharmaceutically acceptable salts exhibit valuable pharmacological properties and, therefore, are useful in medical treatment. In particular, they are useful as sedatives and tranquilizers, since they exhibit central-nervous-system-depressant, anti-convulsive, muscle-relaxant, anxiety-relieving and sedative activities in animals as is indicated in the standard tests described below. Furthermore, the compounds according to the present invention are distinguished by a low toxicity. The pharmacological properties of the following compounds have been evaluated in comparison with 7-chloro-2-methylamino-5-phenyl-3H-1,4-benzodiazepine-4-oxide, which is known under the generic name chlordiazepoxide, and is a well-known tranquilizer, which is particularly useful in the treatment of various psychoneuroses and is commercially available under the tradename Librium:

Compound No. 1: 7-chloro-1-methyl-2-carbamoyl-methylene-5-phenyl-1,3-dihydro-2H-1,4-benzodiazepine.

Compound No. 2: 7-chloro-1-methyl-2-carbamoyl-methylene-5-(2'-chlorophenyl)-1,3-dihydro-2H-1,4-benzodiazepine.

Compound No. 3: 7-chloro-1-methyl-2-carbamoyl-methylene-5-(2'-fluorophenyl)-1,3-dihydro-2H-1,4-benzodiazepine.

Compound No. 4: 7-chloro-1-methyl-2-carbamoyl-methylene-5-(2'-trifluoromethylphenyl)-1,3-dihydro-2H-1,4-benzodiazepine.

Compound No. 5: 7-bromo-1-methyl-2-carbamoyl-methylene-5-(2'-chlorophenyl)-1,3-dihydro-2H-1,4-benzodiazepine.

Compound No. 6: 7-bromo-1-methyl-2-carbamoyl-methylene-5-(2'-fluorophenyl)-1,3-dihydro-2H-1,4-benzodiazepine.

Compound No. 7: 7-nitro-1-methyl-2-carbamoyl-methylene-5-(2'-chlorophenyl)-1,3-dihydro-2H-1,4-benzodiazepine.

Comparative Compound: chlordiazepoxide.

The foregoing compounds have been tested by the following test methods:

A. Acute Toxicity

The acute 7-day-toxicity in white NMRI-mice is determined after administration of a single dose of the test compound per os or i.p. to the mice which had not been fed. The calculation of the $LD_{50}$ is carried out by probitanalysis by means of electronic data processing (see L. Cavelli-Sforza, Gustav Fischer-Verlag, Stuttgart, (1964), Grundbegriffe der Biometrie, p. 153). The resulting $LD_{50}$-values are given in Table I below.

TABLE I

| Compound No. | $LD_{50}$ p.o. (mg/kg) | $LD_{50}$ i.p. (mg/kg) |
|---|---|---|
| 1 | >1470 | 288 |
| 2 | >1000 | 410 |
| 3 | >1470 | 572 |
| 4 | >1470 | 287 |
| 5 | >1470 | >1600 |
| 6 | >1470 | 574 |
| 7 | >1470 | not determined |
| comparison | 903 | 300 |

B. Anti-convulsive activity against pentetrazole-induced spasms

The protective effect of the test compounds against convulsion is determined after oral application to groups of six (6) mice each. 60 minutes after application of the test compounds, a doses of 100 mg/kg of pentetrazole is subcutaneously injected. The occurrance of clonic and tonic convulsions is observed during a total period of 45 minutes. the protective effect of the test compounds against convulsion is determined by comparison with simultaneously performed tests in control-animals. The effective dose $ED_{50}$ is calculated from the probitlogarithmic dosage curves (according to a modified method disclosed by J. E. Blum et al, Arzneimittel-Forsch. 23, 377 (1973)). The resulting $ED_{50}$-values are given in Table II below.

TABLE II

| Compound No. | Inhibition of Pentetrazole-induced convulsions $ED_{50}$ (mg/kg) |
|---|---|
| 1 | 2.4 |
| 2 | 0.1 |
| 3 | 0.4 |
| 4 | 0.3 |
| 5 | 0.3 |
| 6 | 0.4 |
| 7 | 1.0 |
| comparison | 5.0 |

The results which are obtained according to the above method, provide an indication of the anti-convulsive activity of the test compounds. In the pharmacological art, it is well-known that this anti-convulsive activity in animals is an important criterion for evaluating the clinical tranquilizer activity of compounds (see A. Suria and E. Costa, Journal de Pharmacologie, Suppl. No. 1, 5, 94 (1974) and G. Zbinden and L. O. Randall, Advances in Pharmacol. 5, 257, (1967)). The test results given in Table II show a clear superiority of the compounds according to the present invention as compared to chlordiazepoxide.

C. Evaluation of central-nervous-system-depressant properties (prolongation of hexobarbital-induced effect in mice)

The test compounds are orally applied to mice. Additionally, a dose of 64 mg/kg of hexobarbital is injected, i.v., into the animals 30 minutes after application of the test compound. The point of time at which the animals lie down on their side and the duration of this side-posture are determined and are compared with the postural behavior of animals which are treated only with hexobarbital. The $ED_{50}$ is defined as the dose which causes 50% of the animals to maintain the side-wise posture for a period of time which is 4 times as long as the period of time during which the control animals remain in their side-wise lying posture (see J. W. Kemp, M. Tannhaeuser and E. A. Swinyard, Arch. int. Pharmacodyn. 193 (1971), p. 37–47). The resulting $ED_{50}$-values are given in Table III below.

TABLE III

| Compound No. | Prolongation of hexobarbital-induced sleep in mice $ED_{50}$ (mg/kg) | Inhibition of isolation-induced aggressiveness in mice $ED_{50}$ (mg/kg) | |
| --- | --- | --- | --- |
| | | 30' | 60' |
| 1 | 3.2 | 12.2 | 9.6 |
| 2 | 5 | 2.2 | 3.4 |
| 3 | 1.6 | 2.1 | 3.9 |
| 4 | 3.1 | 31.1 | 31.1 |
| 5 | 1.3 | 5.4 | 4.6 |
| 6 | 2.6 | 4.8 | 5.7 |
| 7 | 2.5 | not determined | |
| comparison | 6 | 60 | 47 |

D. Evaluation of anti-aggressive and anxiety-relieving activity (inhibition of the isolation-induced aggressiveness in mice)

Prior to carrying out the test, the mice are kept in strict isolation in single cages for a period of 4 weeks. After this period of isolation, mice which have been kept isolated spontaneously attack other mice which are introduced into their cage and had not been previously isolated. The test compounds are orally administered to the isolated mice and after a period of 30 minutes or 60 minutes after application, the dose which leads to a 50% reduction of the aggressive behavior is determined (according to a modified method described by Weischer and Opitz, Arch. int. Pharmacodyn. 195, 252 (1972)). The results which are obtained in this test are a valid indication of the activity of the tested compounds in relieving anxiety and stress-induced tensions. The resulting $ED_{50}$-values are given in Table III above.

The $ED_{50}$-values in Table III show superior sedative and anti-aggressive activities of the compounds according to the present invention as compared to chlordiazepoxide.

The results which are given in Tables II and III indicate that the compounds according to the present invention possess good anxiety- and stress-relieving properties. In the foregoing pharmacological tests the compounds according to the present invention exhibit a superior activity as compared with the medically used chlordiazepoxide.

Due to their pharmacological activities which are shown in the foregoing pharmacological tests in animals, the compounds of formula I are useful as psychosedative agents which can be used for example as sedatives and tranquilizers in the treatment of states of tension, excitement and agitation, and in the treatment of neuroses.

For the above-mentioned uses, the administered doses can vary considerably depending on the type of the compound, the mode of administration, the treated conditions and the therapy which is desired.

These dosages can be administered enterally, preferably orally, or parenterally. For example, daily oral doses for larger mammals can be chosen between 1 and 200 mg. For the above described medical application, the compounds of formula I can be applied in form of free bases or in form of pharmaceutical acceptable acid-addition-salts, i.e. salts of such acids, the anions of which are non-toxic at the required dosage-levels. Advantageously, such acids are chosen which can be readily crystallized are are not or only slightly hygroscopic. Examples of acids which are suitable for salt-formation with compounds of formula I are the following: hydrochloric acid, hydrobromic acid, sulfuric acid, methylsulfonic acid, ethylsulfonic acid, benzenesulfonic acid, p-toluenesulfonic acid, citric acid, acetic acid, lactic acid, succinic acid, maleic acid, fumaric acid, malic acid, tartaric acid, benzoic acid, phenylacetic acid, or mandelic acid.

According to a feature of the present invention there are further provided pharmaceutical compositions containing at least one of the compounds of formula I or their pharmaceutically acceptable salts. The compositions may take the form of solid or liquid formulation for enteral, preferably oral, or for parenteral administration. The pharmaceutical composition may comprise from about 0.5 to about 200 mg of the pharmacologically active compound of formula I per single-dosage-unit, whereby the single dosage may vary depending on the individual requirements of the treated species and conditions. Formulations for parenteral application usually contain a lower amount of the pharmacologically active compound than formulations for oral application. The compound of formula I may be applied alone or in combination with pharmaceutical acceptable carrier materials and/or adjuvants in many different dosage forms. For example, formulations for oral application may be in the form of tablets, capsules, powders, granulates, emulsions, suspensions, and the like. Solid formulations may comprise a conventional pharmaceutically acceptable inorganic carrier material such as talcum or an organic carrier material such as lactose or starch. Conventional pharmaceutical adjuvants such as magnesium stearate (a lubricant) may also be included. Liquid formulations such as solutions, suspensions, or emulsions may comprise conventional pharmaceutical diluents such as water, vaseline, suspending agents such as polyoxyethylene glycole and the like. Furthermore, conventional adjuvants such as preserving agents, stabilizing agents, and emulsifiers may be added.

The following examples are intended to illustrate the preparation of new compounds of formula I and of pharmaceutical compositions thereof, but are not intended to limit the scope of the present invention in any way.

The chemical structure of the new compounds has been verified by spectroscopic analysis, in particular by exact analysis of the NMR-spectra.

EXAMPLE 1

A. Preparation of 7-chloro-1-methyl-2-cyanomethylene-5-phenyl-1,3-dihydro-2H-1,4-benzodiazepine 50 g of 7-chloro-1-methyl-2-cyanomethyl-5-phenyl-2,3-dihydro-1H-1,4-benzodiazepine (which has been prepared from 7-chloro-1-methyl-2-chloromethyl-5-phenyl-2,3-dihydro-1H-1,4-benzodiazepine and potassiumcyanide according to the method disclosed in the German Offenlegungsschrift No. 2,221,558) are dissolved in 350 ml of glacial acetic acid. Into this solution, 65 ml of a solution of 66.8 g of chromic acid and 57.5 ml of concentrated sulfuric acid in 250 ml of water are introduced drop-wise at a temperature of 13° C. The reaction-temperature of about 13° C. is subsequently maintained for another 3 hours. Then the reaction-mixture is poured into 1 liter of ice-water and the raw product is extracted therefrom with chloroform. The organic phase is separated and washed with a diluted sodium hydroxide solution and then with water and is subsequently dried over sodium sulfate. After filtration and evaporation of the solvent under vacuum, the resulting residue is crystallized from ethanol. 32.3 g of 7-chloro-1-methyl-2-cyanomethylene-5-phenyl-1,3-dihydro-2H-1,4-benzodiazepine, having a melting point of 225° to 227° C., are obtained.

IR-spectrum (KBr): 2198 cm$^{-1}$ (>C=CH—CN)

B. Preparation of 7-chloro-1-methyl-2-carbamoylmethylene-5-phenyl-1,3-dihydro-2H-1,4-benzodiazepine 15.2 g of the 7-chloro-1-methyl-2-cyanomethylene-5-phenyl-1,3-dihydro-2H-1,4-benzodiazepine obtained in Example 1 A are subsequently portion-wise introduced into 80 ml of concentrated sulfuric acid under stirring, and the resulting suspension is slowly heated up to a temperature of 50° C. until a clear solution is formed. Subsequently, the solution is maintained at a temperature of 50° C. for 1 hour. After cooling, the solution is worked-up by pouring it on ice, neutralizing the sulfuric acid with diluted potassium hydroxide solution and extracting the raw product with methylenechloride. The organic phase is separated, washed with water until neutral reaction of the washing-water, and dried over sodium sulfate. After filtration and evaporation of the solvent a residue is obtained which is re-crystallized from ethanol. 11 g of 7-chloro-1-methyl-2-carbamoylmethylene-5-phenyl-1,3-dihydro-2H-1,4-benzodiazepine, having a melting point of 179° to 181° C., are obtained.

Empirical formula: $C_{18}H_{16}ClN_3O \cdot 0.4$ mole $C_2H_5OH$

| Elemental analysis: | C | H | N | Cl |
|---|---|---|---|---|
| calculated %: | 65.76 | 5.36 | 12.15 | 10.25 |
| found %: | 65.64 | 5.17 | 11.85 | 10.44 |

EXAMPLE 2

A. Preparation of 7-chloro-1-methyl-2-cyanomethylene-5-(2'-chlorophenyl)-1,3-dihydro-2H-1,4-benzodiazepine 16 g of chromic acid are added portion-wise to a solution to 66.4 g of 7-chloro-1-methyl-2-cyanomethyl-5-(2'-chlorophenyl)-2,3-dihydro-1H-1,4-benzodiazepine in 250 ml of glacial acetic acid and 125 ml of concentrated hydrochloric acid at a temperature of between 10° and 15° C. After a reaction-period of 1 hour, the reaction-mixture is poured onto ice and is extracted with chloroform. The combined chloroform-extracts are washed to neutral reaction with sodium bicarbonate solution and dried over sodium sulfate. The solvent is evaporated under vacuum, the resulting residue is dissolved in acetone and a solution of 40 g of p-toluenesulfonic acid in acetone is added. The resulting precipitate is filtered-off under suction and is stirred-up in a mixture of diluted sodium hydroxide solution and chloroform. The chloroform-phase is separated, dried over sodiumsulfate, and the solvent is evaporated under vacuum. The resulting residue is re-crystallized from isopropanol. 7-chloro-1-methyl-2-cyanomethylene-5-(2'-chlorophenyl)-1,3-dihydro-2H-1,4-benzodiazepine, having a melting point of 162° to 165° C., is obtained.

IR-spectrum (KBr): 2193 cm$^{-1}$ (>C=CH—CN)

B. Preparation of 7-chloro-1-methyl-2-carbamoylmethylene-5-(2'-chlorophenyl)-1,3-dihydro-2H-1,4-benzodiazepine 5.4 g of 7-chloro-1-methyl-2-cyanomethylene-5-(2'-chlorophenyl)-1,3-dihydro-2H-1,4-benzodiazepine are introduced portion-wise into 26 ml of concentrated sulfuric acid and are dissolved therein while the mixture is slowly heated-up to a temperature of 50° C. The solution is kept at a temperature of 50° C. for 1 more hour. For working-up after cooling the solution is poured onto ice, the sulfuric acid is neutralized with diluted sodiumhydroxide solution and the raw product is extracted with methylenechloride. The organic phase is separated, washed with water to neutral reaction and dried over sodium sulfate. After filtration and evaporation of the solvent under vacuum, a residue is obtained and is crystallized by trituration with ether. After re-crystallization from ethanol, 7-chloro-1-methyl-2-carbamoylmethylene-5-(2'-chlorophenyl)-1,3-dihydro-2H-1,4-benzodiazepine, having a melting point of 212° to 217° C., is obtained.

Empirical formula: $C_{18}H_{15}Cl_2N_3O$

| Elemental analysis: | C | H | N | Cl |
|---|---|---|---|---|
| calculated %: | 60.01 | 4.19 | 11.66 | 19.68 |
| found %: | 59.73 | 4.26 | 11.42 | 19.43 |

In the same manner as described in the foregoing examples, the following compounds can be prepared:

EXAMPLE 3

According to the method of Example 1, however using 7-bromo-1-methyl-2-cyanomethyl-5-(2'-chlorophenyl)-2,3-dihydro-1H-1,4-benzodiazepine as starting material, the following compounds are obtained:

3a.   7-bromo-1-methyl-2-cyanomethylene-5-(2'-chlorophenyl)-1,3-dihydro-2H-1,4-benzodiazepine, melting point 178°-179° C., and 3b.   7-bromo-1-methyl-2-carbamoylmethylene-5-(2'-chlorophenyl)-1,3-dihydro-2H-1,4-benzodiazepine, melting point 110°-115° C. under decomposition (containing ¾ moles of acetone).

EXAMPLE 4

According to the method of Example 2, however using 7-bromo-1-methyl-2-cyanomethyl-5-(2'-fluorophenyl)-2,3-dihydro-1H-1,4-benzodiazepine as starting material, the following compounds are obtained:

4a. 7-bromo-1-methyl-2-cyanomethylene-5-(2'-fluorophenyl)-1,3-dihydro-2H-1,4-benzodiazepine, melting point 167°–168° C., and 4b. 7-bromo-1-methyl-2-carbamoylmethylene-5-(2'-fluorophenyl)-1,3-dihydro-2H-1,4-benzodiazepine, melting point 154°–155° C. (containing ½ moles of acetone).

EXAMPLE 5

According to the method of Example 2, however using 7-chloro-1-methyl-2-cyanomethyl-5-(2'-fluorophenyl)-2,3-dihydro-1H-1,4-benzodiazepine as starting material, the following compounds are obtained:

5a. 7-chloro-1-methyl-2-cyanomethylene-5-(2'-fluorophenyl)-1,3-dihydro-2H-1,4-benzodiazepine, melting point 160°–162° C., and 5b. 7-chloro-1-methyl-2-carbamoylmethylene-5-(2'-fluorophenyl)-1,3-dihydro-2H-1,4-benzodiazepine, melting point 162°–163° C. (containing ½ moles of $H_2O$ and ⅓ moles of acetone).

EXAMPLE 6

According to the method of Example 2, however using 7-nitro-1-methyl-2-cyanomethyl-5-(2'-chlorophenyl)-2,3-dihydro-1H-1,4-benzodiazepine as starting material, the following compounds are obtained:

6a. 7-nitro-1-methyl-2-cyanomethylene-5-(2'-chlorophenyl)-1,3-dihydro-2H-1,4-benzodiazepine, melting point 83°–90° C., and 6b. 7-nitro-1-methyl-2-carbamoylmethylene-5-(2'-chlorophenyl)-1,3-dihydro-2H-1,4-benzodiazepine, melting point 211°–214° C.

EXAMPLE 7

According to the method of Example 1, however using 7-chloro-1-methyl-2-cyanomethyl-5-(2'-trifluoromethylphenyl)-2,3-dihydro-1H-1,4-benzodiazepine as starting material, the following compounds are obtained:

7a. 7-chloro-1-methyl-2-cyanomethylene-5-(2'-trifluoromethylphenyl)-1,3-dihydro-2H-1,4-benzodiazepine, melting point 125°–130° C., and 7b. 7-chloro-1-methyl-2-carbamoylmethylene-5-(2'-trifluoromethylphenyl)-1,3-dihydro-2H-1,4-benzodiazepine, melting point 101°–105° C.

EXAMPLE 8

According to the method of Example 1, however using 7-bromo-1-methyl-2-cyanomethyl-5-(2'-trifluoromethylphenyl)-2,3-dihydro-1H-1,4-benzodiazepine as starting material, the following compounds are obtained:

8a. 7-bromo-1-methyl-2-cyanomethylene-5-(2'-trifluoromethylphenyl)-1,3-dihydro-2H-1,4-benzodiazepine, melting point 128°–130° C., and 8b. 7-bromo-1-methyl-2-carbamoylmethylene-5-(2'-trifluoromethylphenyl)-1,3-dihydro-2H-1,4-benzodiazepine, melting point 115°–120° C.

EXAMPLE 9

Tablets

Tablets, having the following composition per tablet, are prepared as follows:

| | |
|---|---|
| 7-chloro-1-methyl-2-carbamoyl-methylene-5-phenyl-1,3-dihydro-2H-1,4-benzodiazepine | 10 mg |
| corn starch | 60 mg |
| lactose | 130 mg |
| gelatin (10% solution) | 6 mg |

The active ingredients, corn starch, and lactose, are mixed with a 10% solution of gelatin to form a paste. The paste is comminuted into a granulate, the granulate is placed onto a suitable metal sheet and is dried at a temperature of 45° C. The dried granulate is passed through a comminution-apparatus and introduced into a mixer where it is mixed with the following components:

| | |
|---|---|
| talcum | 5 mg |
| magnesium stearate | 5 mg |
| corn starch | 9 mg | and then is pressed into tablets having a weight of 225 mg.

EXAMPLE 10

Suppositories

Suppositories are prepared using the following ingredients per a 2 g suppository:

| | |
|---|---|
| 7-chloro-1-methyl-2-carbamoyl-methylene-5-phenyl-1,3-dihydro-2H-1,4-benzodiazepine | 10 mg |
| cocoa butter | 1990 mg |

The active ingredient and the finely ground suppository mass are thoroughly mixed and then molten. The molt is kept homogenous by means of stirring and is poured into 2 g suppository molds.

EXAMPLE 11

A solution for parenteral injection is prepared containing the following ingredients per ml.:

| | |
|---|---|
| 7-chloro-1-methyl-2-carbamoylmethylene-5-phenyl-1,3-dihydro-2H-1,4-benzodiazepine | 5 mg |
| dimethylacetamide | 10% |
| propyleneglycol | 50% |

The active ingredient is dissolved in dimethylacetamide and benzylalcohol, propyleneglycol, ethanol, and water are added to the solution. The solution is filtrated through a cone-shaped filter and filled into suitable ampoules which are closed and sterilized.

EXAMPLE 12

According to the methods described in Example 9 to 11, tablets, suppositories or solutions for parenteral injection are prepared, however using as the active ingredient 7-chloro-1-methyl-2-carbamoylmethylene-5-(2'-chlorophenyl)-1,3-dihydro-2H-1,4-benzodiazepine.

What is claimed is:

1. A compound selected from the group of 1,4-benzodiazepines of the formula I

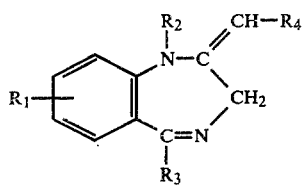

wherein
- $R_1$ represents hydrogen, halogen, or nitro;
- $R_2$ represents hydrogen, or lower alkyl;
- $R_3$ represents phenyl, or phenyl which is substituted by halogen or trifluoromethyl; and
- $R_4$ represents cyano or carbamoyl and pharmaceutically-acceptable acid addition salts thereof.

2. The compound as defined in claim 1, wherein $R_1$ represents chlorine, bromine, or nitro.

3. The compound as defined in claim 2, wherein $R_1$ is in 7-position of the 1,4-benzodiazepine.

4. The compound as defined in claim 1, wherein $R_2$ is methyl.

5. The compound as defined in claim 1, wherein $R_3$ represents phenyl, o-chlorophenyl, o-fluorophenyl, or o-trifluoromethylphenyl.

6. The compound as defined in claim 1, wherein $R_4$ is cyano.

7. The compound as defined in claim 1, wherein $R_4$ is carbamoyl.

8. The compound as defined in claim 7, wherein $R_1$ represents chlorine, bromine, or nitro and is in 7-position of the 1,4-benzodiazepine, $R_2$ is methyl, and $R_3$ represents phenyl, o-chlorophenyl, o-fluorophenyl, or o-trifluoromethylphenyl.

9. The compound as defined in claim 1 which is 7-chloro-1-methyl-2-carbamoylmethylene-5-phenyl-1,3-dihydro-2H-1,4-benzodiazepine and its pharmaceutically-acceptable acid addition salts.

10. The compound as defined in claim 1, which is 7-chloro-1-methyl-2-carbamoylmethylene-5-(2'-chlorophenyl)-1,3-dihydro-2H-1,4-benzodiazepine and its pharmaceutically-acceptable acid addition salts.

11. The compound as defined in claim 1, which is 7-bromo-1-methyl-2-carbamoylmethylene-5-(2'-chlorophenyl)-1,3-dihydro-2H-1,4-benzodiazepine and its pharmaceutically-acceptable acid addition salts.

12. The compound as defined in claim 1, which is 7-bromo-1-methyl-2-carbamoylmethylene-5-(2'-fluorophenyl)-1,3-dihydro-2H-1,4-benzodiazepine and its pharmaceutically-acceptable acid addition salts.

13. The compound as defined in claim 1, which is 7-chloro-1-methyl-2-carbamoylmethylene-5-(2'-fluorophenyl)-1,3-dihydro-2H-1,4-benzodiazepine and its pharmaceutically-acceptable acid addition salts.

14. The compound as defined in claim 1, which is 7-nitro-1-methyl-2-carbamoylmethylene-5-(2'-chlorophenyl)-1,3-dihydro-2H-1,4-benzodiazepine and its pharmaceutically-acceptable acid addition salts.

15. The compound as defined in claim 1, which is 7-chloro-1-methyl-2-carbamoylmethylene-5-(2'-trifluoromethylphenyl)-1,3-dihydro-2H-1,4-benzodiazepine and its pharmaceutically-acceptable acid addition salts.

16. The compound as defined in claim 1, which is 7-bromo-1-methyl-2-carbamoylmethylene-5-(2'-trifluoromethylphenyl)-1,3-dihydro-2H-1,4-benzodiazepine and its pharmaceutically-acceptable acid addition salts.

17. A process for preparing the 1,4-benzodiazepines of the formula I as defined in claim 1 wherein $R_1$, $R_2$, and $R_3$ are as defined in claim 1, and $R_4$ is cyano which comprises the step of oxidizing a compound of formula II

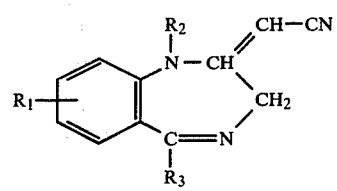

wherein
- $R_1$ represents hydrogen, halogen, or nitro;
- $R_2$ represents hydrogen, or lower alkyl; and
- $R_3$ represents phenyl, or phenyl which is substituted by halogen or trifluoromethyl in an acidic reaction mixture with an oxidizing agent comprising a chromium-VI-compound which is chromium-VI-oxide, chromic acid, or a mixture thereof at least partially dissolved in an acidic solvent to form a compound of formula Ia

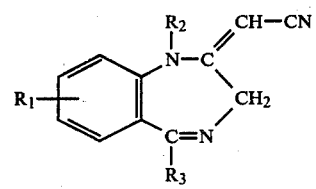

wherein
- $R_1$ represents hydrogen, halogen, or nitro;
- $R_2$ represents hydrogen, or lower alkyl; and
- $R_3$ represents phenyl, or phenyl which is substituted by halogen or trifluoromethyl.

18. The process as defined in claim 17, which further comprises the step of hydrolyzing the compound of formula Ia to obtain a compound of formula Ib

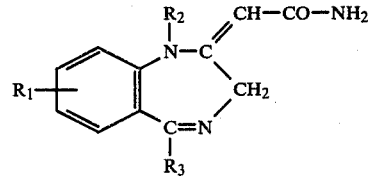

wherein
- $R_1$ represents hydrogen, halogen, or nitro;
- $R_2$ represents hydrogen, or lower alkyl; and
- $R_3$ represents phenyl, or phenyl which is substituted by halogen or trifluoromethyl.

19. A pharmaceutically composition comprising a tranquilizing effective amount of a least one pharmacologically-active compound as defined in claim 1 and a pharmaceutically acceptable diluent.

* * * * *

UNITED STATES PATENT OFFICE
CERTIFICATE OF CORRECTION

Patent No. 4,170,649  Dated October 9, 1979

Inventor(s) Hans LIEPMANN, Rolf HUESCHENS, Wolfgang MILKOWSKI, Horst ZEUGNER, Renke BUDDEN and Jacqueline BAHLSEN It is certified that error appears in the above-identified patent and that said Letters Patent are hereby corrected as shown below:

IN THE SPECIFICATION

Column 2, formula II, kindly delete the entire formula and insert instead

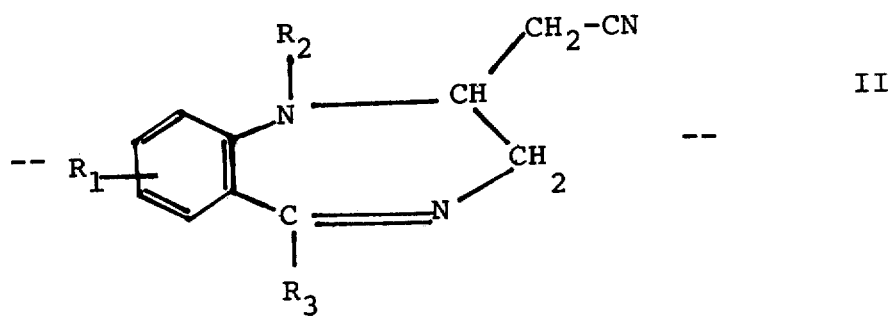

-- II --

UNITED STATES PATENT OFFICE
CERTIFICATE OF CORRECTION

Patent No. 4,170,649      Dated October 9, 1979

Inventor(s) Hans LIEPMANN, Rolf HUESCHENS, Wolfgang MILKOWSKI, Horst ZEUGNER, Renke BUDDEN and Jacqueline BAHLSEN It is certified that error appears in the above-identified patent and that said Letters Patent are hereby corrected as shown below:

<u>IN THE CLAIMS</u>

Column 14, formula II, kindly delete the entire formula and insert instead

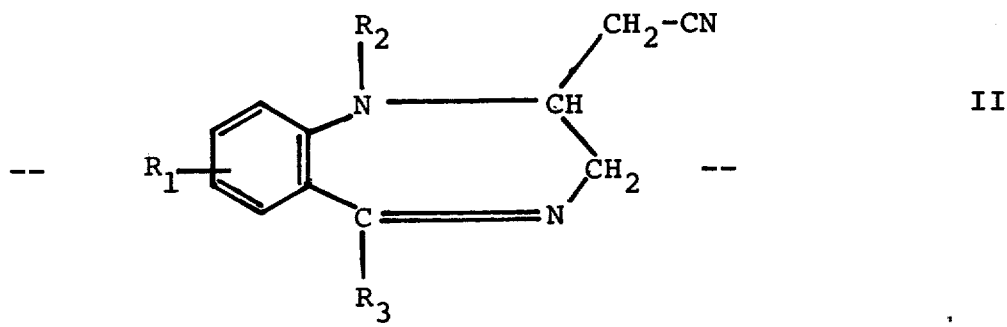

Signed and Sealed this

Twenty-second Day of April 1980

[SEAL]

Attest:

SIDNEY A. DIAMOND

Attesting Officer     Commissioner of Patents and Trademarks